(12) United States Patent
Davis

(10) Patent No.: US 9,126,094 B1
(45) Date of Patent: Sep. 8, 2015

(54) ELECTRONIC TRACK BATON DEVICE

(71) Applicant: Donnell A. Davis, Bowie, MD (US)

(72) Inventor: Donnell A. Davis, Bowie, MD (US)

(*) Notice: Subject to any disclaimer, the term of this patent is extended or adjusted under 35 U.S.C. 154(b) by 0 days.

(21) Appl. No.: 14/303,463

(22) Filed: Jun. 12, 2014

(51) Int. Cl.
*A63B 24/00* (2006.01)
*A63B 71/06* (2006.01)
*G07C 1/24* (2006.01)
*A63B 69/00* (2006.01)

(52) U.S. Cl.
CPC .............. *A63B 71/06* (2013.01); *A63B 69/0028* (2013.01); *G07C 1/24* (2013.01)

(58) Field of Classification Search
CPC ....... A63B 71/06; A63B 69/0028; G07C 1/24
See application file for complete search history.

(56) References Cited

U.S. PATENT DOCUMENTS

| 7,066,864 | B2 | 6/2006 | Olkkonen | |
|---|---|---|---|---|
| 7,294,777 | B2* | 11/2007 | Hofmeister et al. | 84/615 |
| 8,021,281 | B2* | 9/2011 | Forsell et al. | 482/84 |
| 8,445,769 | B2* | 5/2013 | Takahashi | 84/737 |
| 2013/0059696 | A1 | 3/2013 | Hijmans et al. | |

* cited by examiner

*Primary Examiner* — Glenn Richman
(74) *Attorney, Agent, or Firm* — Crossley Patent Law

(57) ABSTRACT

An electronic track baton device having fully cooperating functions for a plurality of users, including split timing, magnetometer, speedometer, pedometer, accelerometer, heart rate monitor, stride measure, multi-user timer, audio feedback, EPROM, RFID, gyroscope, GUI, capacitive sensors, a speaker/microphone, a clock, a USB port, a WiFi, and a Bluetooth.

4 Claims, 10 Drawing Sheets

ELECTRONIC TRACK BATON DEVICE

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Various types of electronic human performance recording, interaction and measurement apparatuses are known in the prior art. However, what is needed is an electronic track baton device that provides user feedback and input, information gathering and transference, and interactive capability with other existing electronic media apparatuses.

FIELD OF THE INVENTION

The present invention relates to devices and methods for receiving, recording and displaying information relating to physical activities, and more particularly, to an electronic track baton device that provides electronic information uptake and user feedback as well as interaction with other existing electronic apparatuses and users.

SUMMARY OF THE INVENTION

The general purpose of the present electronic track baton device, described subsequently in greater detail, is to provide an electronic track baton device that has many novel features that result in an electronic track baton device that is not anticipated, rendered obvious, suggested, or even implied by prior art, either alone or in combination thereof.

To accomplish this, the electronic track baton device comprises a hollow cylindrical baton having a first end spaced apart from a second end, a first linear member selectively separable from a second linear member, each of the linear members and extended from the first end to the second end, a length no greater than ½ inches and a constant circumference of at least 4 inches but no greater than 5 inches. A GUI (Graphic User Interface) is disposed equidistantly between the first end and the second end within the first linear member. A touch sensor is disposed within the GUI. A plurality of externally sensitive capacitor sensors is provided. One capacitor sensor disposed between the GUI and the first end of each of the first linear member and the second linear member, respectively. One capacitor sensor is disposed between the GUI and the second end of each of the first linear member and the second linear member, respectively. The capacitor sensors comprise a biometric sensor switching. An existing metal in communication with the capacitor sensors becomes an extension of the capacitor sensors. A proximity detector switch is in operational communication with the capacitor sensors.

A plurality of interactive electronic components is disposed within the hollow cylindrical baton. The electronic components are in operational communication and are in operational communication with the GUI and the capacitor sensors. A power button and a USB port are disposed within the second end. The remaining electronic components are disposed within an approximate center of the hollow cylindrical baton. The remaining electronic components comprise a plurality of FPC (Flexible Printed Circuits), a speaker/microphone, a vibration and tactile sensor, an EPROM disposed within the CPU, an RFID (Radio Frequency Identification), a transceiver, a 3-axis gyroscope, a heart rate monitor, a magnetometer, a multi-user timer, a rechargeable battery, a speedometer, a pedometer, a stride measure, an ANT+ wireless sensor network protocol, a Wi-Fi, a Bluetooth, a biometric sensor switching, a 3-axis accelerometer, an electrode, and a crystal oscillator clock, a programmable logic controller, and an input/output bridge.

The track baton device is configured to interact with various existing media via the Bluetooth, the WiFi, the transceiver, and the USB port. The device is importantly configured to provide split timing for a plurality of users via the multi-user timer. A plurality of light sources for the GUI include but are not limited to a Liquid Crystal Display (LCD), a Light-Emitting Diode (LED), and an Organic Light-Emitting Diode (OLED). The GUI indicates various features of the electronic track baton device that are customizable by any user. The touch sensor disposed in the GUI provides for user chosen operations. The GUI provides a plurality of options including an on/off, a menu, a mode, a further plurality of options, which include a calibration logic, an athlete, a coaching, a sensory feedback, and an access to a plurality of various existing media. The on/off provides for on/off via a plurality of taps and swipes. The hollow cylindrical baton's power button is activated to provide communication with the rechargeable battery to operate the GUI. The hollow cylindrical baton's power button has a dual functionality as a touchscreen toggle button.

The mode provides for an activation, a deactivation, and a plurality of display modes of operation for the electronic track baton device. The modes include a speaker/microphone, a vibration and tactile sensor, a pedometer, a speedometer, a stride measure, and a multi-user timer.

The calibration logic provides for an adjustment of the hand detection sensitivity for the proximity detector switch, the capacitive sensors, the touch sensor, and the heart rate sensor. Further, a manual timing refresh calibration operation is provided that prepares the hollow cylindrical baton's recording mode for a race and an exercise wherein any user can reset the multi-user timer to a zero which is confirmed by the baton's speaker and the vibration unit. The user simultaneously holds the capacitive sensors located on both ends of the hollow cylindrical baton device for a predetermined time for timing reset. The device includes the wireless transceiver for facilitating wireless communications with existing cooperative software and devices. The CPU allows the relevant data to be accessible and linked to several existing interactive programs via the device's multiple wireless capabilities (e.g., ANT+, RFID, Bluetooth, Wi-Fi). These existing devices and capabilities include a smartphone display, mobile applications, analytics software, game theory, split and biometric website, coaching software, eyewear software, and video recording devices. For illustration, a mobile communication link via Bluetooth will provide athletes an interactive experience.

The electronic track baton device will wirelessly acquire biomechanical data and then transmit to a point-of-view video recording device such as Google Glass, therein allowing athletes to view a plurality of performance metrics, in real-time, that include but are not limited to meters traveled with corresponding time, speed, heart rate and intensity level.

The GUI interactive touchscreen is used to indicate that the hollow cylindrical baton device is on/off and active for recording mode for each race/exercise.

The CPU executes plurality of instructions and control data among the device's components. The CPU incorporates, a programmable logic controller, an EPROM (Erasable Programmable Read Only Memory) an IO (Input/Output) bridge, a multi-user timer, and a crystal oscillator clock.

The programmable logic controller frees the CPU for time-critical tasks and provides low power consumption. The programmable logic controller's main purpose is to manage the electronic track baton device's electronic decision cycles by starting and stopping a plurality of differing processes.

The EPROM serves as a data acquisition module that retains its data for a minimum of 10 to 20 years and can be read an unlimited number of times. The electronic track baton device stores information about exercise sessions via the CPU and EPROM. This data then can be transferred to an existing mobile device or PC via the micro USB port or wireless connection in order to track user's progress over time. The multi-user provides the stopwatch timer that counts upward from zero to measure elapsed time using the crystal oscillator clock. The crystal oscillator clock is a computer in the form of an integrated circuit operating under a very precise frequency such as 32.678 kHz and provides precise timing within 1/1000th of a second. The multi-user timer is triggered by the motion and touch sensing functions of the device.

The electronic track baton device uses the capacitive sensors capability, the CPU, the proximity detector switch, the touch sensor, and the electrode to achieve the electronic track baton device's biometric sensor switching. The heart rate sensor is used to achieve optimal performance via heart rate training.

The biometric sensor switching serves as an electrical relay touch switch in which the electronic track baton device's internal electronic components can operate between 5 milliseconds (0.005 seconds) and 20 milliseconds (0.02 seconds). The proximity detector switch's purpose is to detect the presence of nearby fingers or hands without any physical contact. The touch sensor determines actual hand contact with the electronic track baton device's surface by measuring the change in an electromagnetic field. The capacitive sensors are constructed of transparent conductive materials, such as Indium Tin Oxide (ITO), a polyester (PET) film layer, or a glass substrate. Projected capacitive technology comprises a matrix of rows and columns of conductive material, etched on a single conductive layer to form a grid pattern of electrodes. The electronic track baton device specifically uses this technology to detect touch by measuring the change of capacitance at an addressable electrode. Thus, the electronic track baton device operates a capacitance touch switch device that needs only one electrode to function. The electrode is an electrical conductor used to make contact with a nonmetallic part of a circuit or object. With present device, when a finger or hand actually touches the electrode embedded electronic track baton device, it disturbs the electromagnetic field and alters the capacitance. This change in capacitance is measured by the CPU, the proximity detector switch, and the touch sensor and converted to detect touch.

With the automated split timing the programmable logic controller operation determines the change in electronic track baton device capacitance. The electronic track baton device uses the CPU, the programmable logic controller, and the proximity detector switch to enhance accuracy as they are used in combination to check against false electronic track baton device exchanges. For example, many users tend to adjusts hands during electronic track baton device exchanges, which in this context can be referred to as "noise." Thus, the electronic track baton device must have hand contact within a predetermined threshold, for example within 5 milliseconds of hand proximity detection to start timing and/or split transition. If not, the timing will start and will continue on the current split in accordance to the process flowchart phases. The electronic track baton device includes heart rate sensors having receptors for detecting electronic cardiac signals in order to get the most effective workout by training at the right intensity level. The heart rate sensor receptors are seamlessly flush with the electronic track baton device surface and use optoelectronics technology. Optoelectronics is the study and application of electronic devices that source, detect and control light. In operation, the CPU acquires cardiac signals generated through the user's provide for the device to achieve optimal performance via heart rate training.

As noted, the electronic track baton device uses a magnetometer, a 3-axis accelerometer, and a 3-axis gyroscope magnetometer to detect movement, ultimately achieving 1:1 motion via six degrees of freedom or XYZ direction measurement, i.e. yaw, pitch, and roll. The magnetometer is used to determine the direction of the magnetic field at a point in space. The magnetometer changes to the magnetic field around the electronic track baton device to identify different gestures made. The 3-axis accelerometer detects relational acceleration along 3-axis and measures the g-force that acts upon it. The 3-axis gyroscope measures or maintains the orientation, based on the principles of angular momentum. The electronic track baton device's operation specifically incorporates existing movement sensor technology such as ANT+ technology. ANT+ is an existing microchip with an interoperability function that is added to the base ANT protocol (an existing proprietary wireless sensor network technology). The accelerometer and gyroscope incorporated in ANT+ are used to measure biometric information calculated based solely on the users start/stop movements when walking, running, or stepping. These features operate similarly to digital devices that display data on exercise equipment such as a treadmill, elliptical, step climber, etc.

In operation, the CPU coupled with supporting CPU code and software is configured to acquire data from the magnetometer and movement sensors. The CPU identifies fluctuations in electronic track baton device swing motions and stride measure to initiate and deactivate the start/stop timing phases of a race. This operation element is critical as the rules of the sport are specific. The electronic track baton device also applies the ANT+ pedometer, speedometer, and stride measure features to accurately measure steps taken and meters/distance traveled to achieve optimal electronic track baton device exchanges in relays, and to determine the most effective/efficient usage of an existing 20-meter baton exchange zone.

The electronic track baton device provides hardware components to include a rechargeable battery to supply power to an entirety of components, capabilities and functions of the baton, the micro USB port to charge the battery and to provide optional access to existing media, the vibration and tactile sensor the and the speaker/microphone.

The electronic track baton device is capable of producing sensory feedback by replicating and simulating select coaching instructions and verbal commands to athletes. As example, the CPU, in communication with the EPROM, is programmed to include vibration and audio prompts for predetermined workouts. The wireless and micro USB port allow connectivity to existing media for multiple external software and coaching options. The electronic track baton device provides user options via the GUI, and the means for activating, deactivating, and displaying modes of operation for the electronic track baton device. The speaker on/off operation is critical as the rules of the sport are specific.

The electronic track baton device provides the wireless transceiver to enable the capabilities of RFID, ANT+, Bluetooth, and Wi-Fi in order to communicate data with other existing media/devices. RFID is the wireless non-contact use of radio-frequency electromagnetic fields to transfer data, for the purposes of identifying and tracking tags attached to objects. The tags contain electronically stored information. The RFID is important as it links each individual electronic track baton device to other existing devices, teams, athletes, coaches. As example, multiple electronic track baton devices can be used simultaneously in the same race. ANT+ wireless capabilities allows for data-transfer for a number of existing devices such as heart rate monitors, speed sensors, cadence sensors, foot pods, power meters, activity monitors, calorimeters, pulse oximeters, and positions tracking devices.

With any user in the starting blocks, as example, the CPU identifies that the electronic track baton device power button is set to the "on" position. The process flow proceeds to a next step. The CPU is now on standby and a state of readiness. The CPU specifically enables the proximity detector switch and the touch sensor. The process flow proceeds to a third step. The CPU monitors the proximity detector switch and the touch sensor. The programmable logic controller is activated and ready to execute instructions regarding capacitive sensors and the electrode. The process flow proceeds to a fourth step. The programmable logic controller sends a signal to the touch sensor and determines whether a user actually touched the electronic track baton device. If it is determined no touch occurred, the process flows back to the third step for continued monitoring. If touch does occur, then the process flow proceeds to a fifth step. The CPU specifically enables the motion sensor detection module. The process flow proceeds to sixth step. Step 6—The CPU acquires the data from the magnetometer and the movement sensors using the ANT+ technology. The process flow proceeds to a seventh step. The CPU monitors the electronic track baton device for changes in any of a plurality of gestures, relational acceleration, orientation, and angular momentum. The programmable logic controller is activated and ready to execute instructions regarding motion tracking. The process flow proceeds to an eighth step.

The programmable logic controller sends a signal to the CPU and determines any fluctuations in electronic track baton device swing motions and stride measurement. If it is determined no movement fluctuations occurred, the process flows back to the seventh step for continued monitoring. If movement fluctuations do occur, then the process flow proceeds to a ninth step. The CPU specifically enables the automated timing sequence module. The process flow proceeds to a tenth step wherein The CPU initiates the crystal oscillator clock and places the multi-user timer on standby and state of readiness. The CPU enables the EPROM and process flow proceeds to an eleventh step.

In the eleventh step the CPU monitors for current touch and movement detection. The CPU also will monitor for any previous data by accessing EPROM data. The programmable logic controller is activated and ready to execute instructions regarding touch and motion tracking. The process flow proceeds to a twelfth step wherein the programmable logic controller sends a signal to the CPU and determines the current state of all touch and movement sensing. If it is determined that any sensor element is missing, the process flows back to the eleventh step for continued monitoring. If all sensor elements are detected, then the process flow proceeds to a thirteenth step wherein the CPU activates the multi-user timer to count upward from zero to measure elapsed time using the crystal oscillator clock. The process flow proceeds to a fourteenth step.

In the fourteenth step, the CPU first initiates the GUI to display timing data on the electronic track baton device within $\frac{1}{1000}$th of a second, then activates the wireless transceiver that allows for automatic real-time tracking via an existing device, then activates the wireless transceiver for facilitating wireless communications with existing cooperative software and devices, and the EPROM stores all statistics. The process flow proceeds to fifteenth step, wherein the CPU enables the multi-user timer for what is known in track events as split timing. The process flow proceeds to a sixteenth step.

In the sixteenth step, the CPU continues to engage the crystal oscillator clock integrated within the device, the multi-user timer, and the EPROM data acquisition module. The process flow proceeds to a seventeenth step during which the CPU will monitor for any previous touch and motion data by accessing the EPROM. The CPU and touch sensor monitor for any change in the electronic track baton device's baseline capacitance. The programmable logic controller is activated and ready to execute instructions regarding change capacitance tracking. The process flow proceeds to an eighteenth step.

In the eighteenth step the programmable logic controller sends a signal to the CPU and determines the current state of baseline capacitance. If it is determined that change in capacitance is outside a predetermined "noise" timing threshold, the process flows back to step 17 for continued monitoring. If the change in capacitance is within the timing threshold, then the process flow proceeds to a nineteenth step.

In the nineteenth step the CPU calculates the split timing based on the change in capacitance. The multi-user timer continues to measure total elapsed time using the crystal oscillator clock. The process flow proceeds to a twentieth step during which the CPU initiates the GUI to display timing data on the electronic track baton device within $\frac{1}{1000}$th of a second, activates the wireless transceiver that provides for communication with existing external media and cooperative devices and automatic, and initiates the EPROM to store all statistics. The process flow proceeds to a twenty first step.

In the twenty first step, the programmable logic controller sends a signal to the CPU and determines the current state of all touch and movement capabilities within the device. If it is determined that all sensor elements are detected, then the process flows back to the seventeenth step for continued capacitance monitoring. If the swing and stride sensor elements are missing, the process flow proceeds to a twenty second step, which is the end of operation.

The external dimensions of the hollow cylindrical baton device are extremely important, as is the hollow feature, as the rules of the sport are specific.

Thus has been broadly outlined the more important features of the present electronic track baton device so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1A:
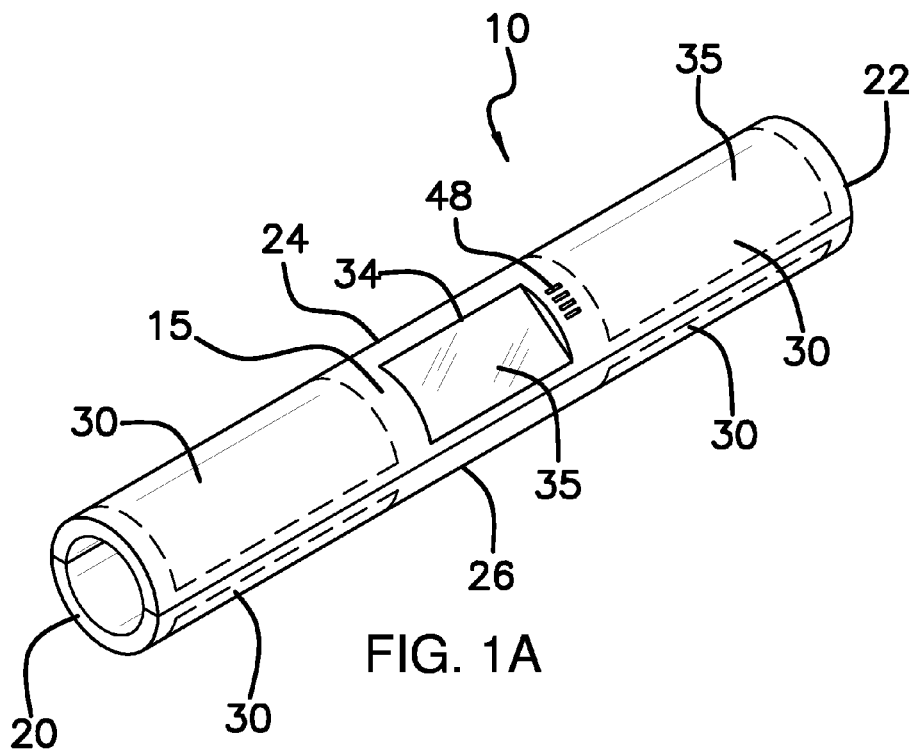
FIG. 1A is a perspective view of an electronic track baton device.
Figure 3:
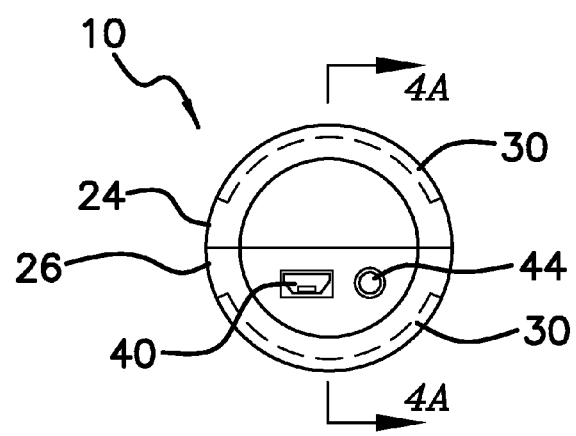
FIG. 3 is an end view of the electronic track baton device.
Figure 1B:
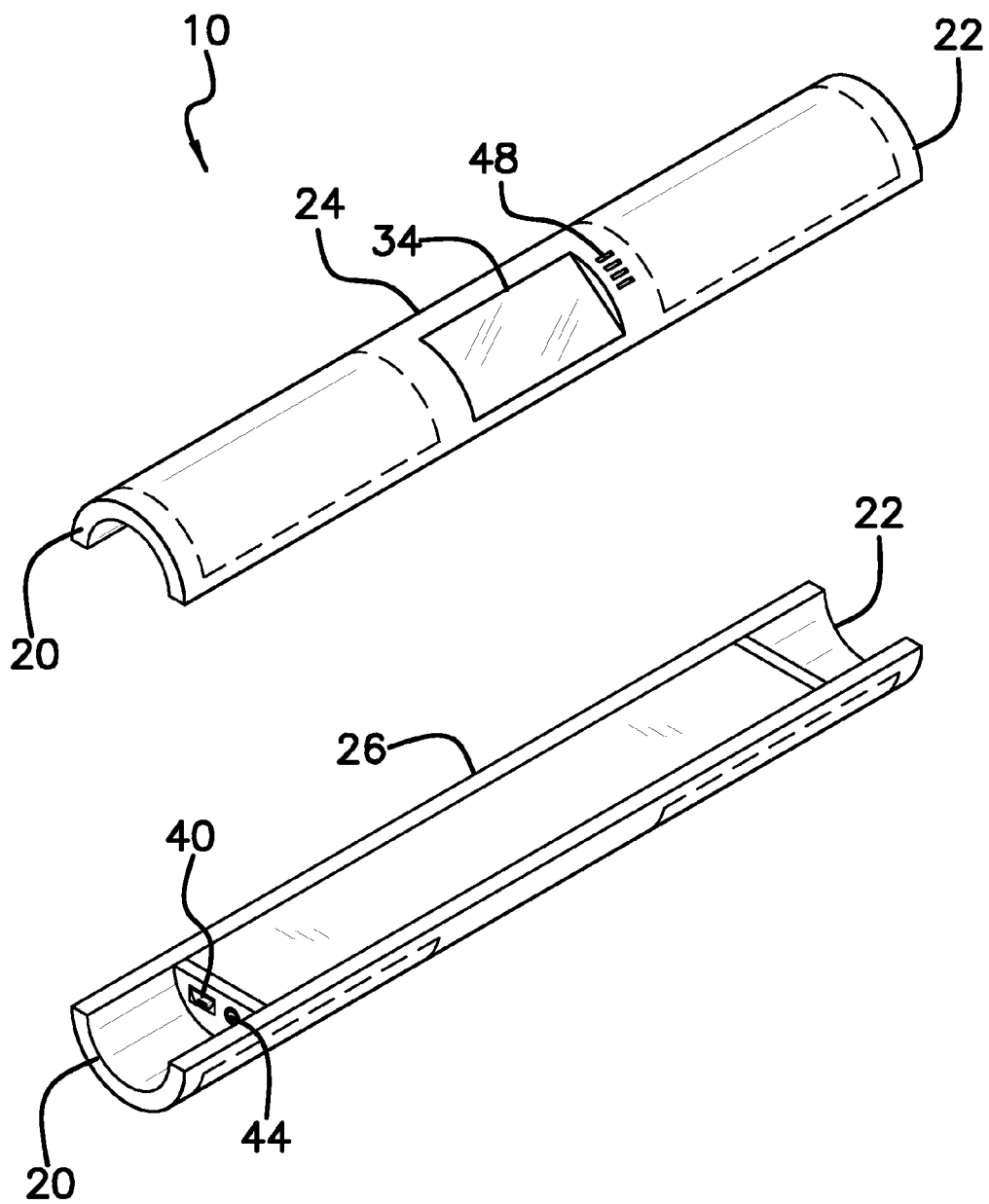
FIG. 1B is an exploded view of FIG. 1A.
Figure 2A:
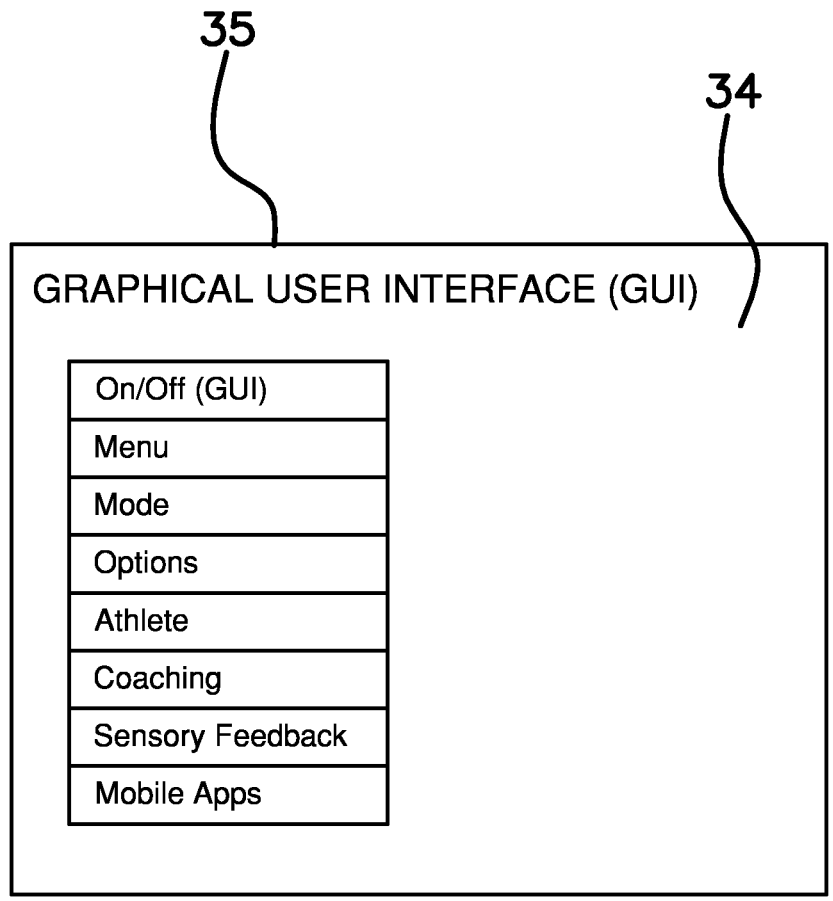
FIG. 2A is a block diagram of a GUI.
Figure 4A:
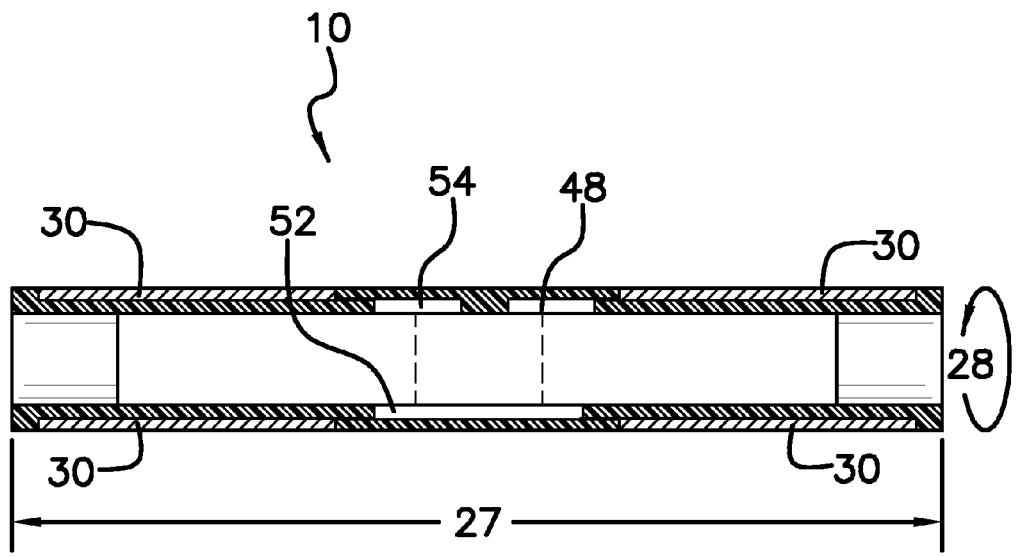
FIG. 4A is a cross sectional view of FIG. 3, taken along the line 4A.
Figure 4B:
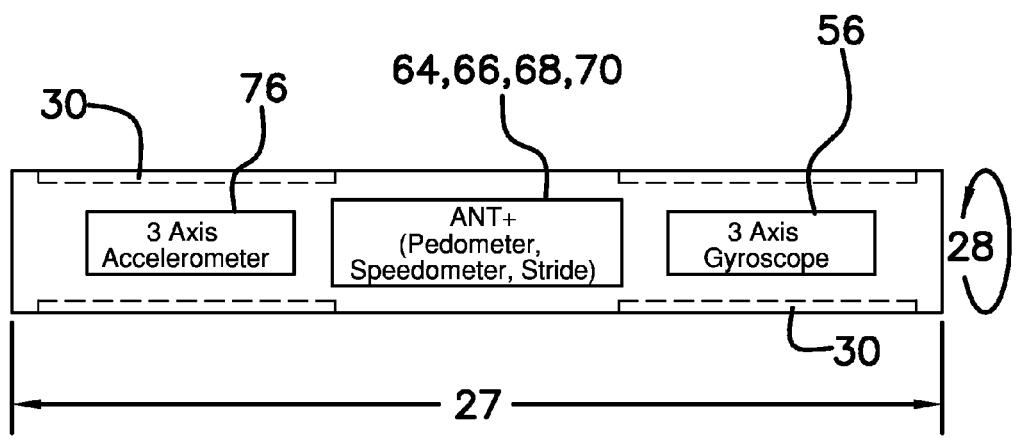
FIG. 4B is a side view of a plurality of elements.
Figure 5:
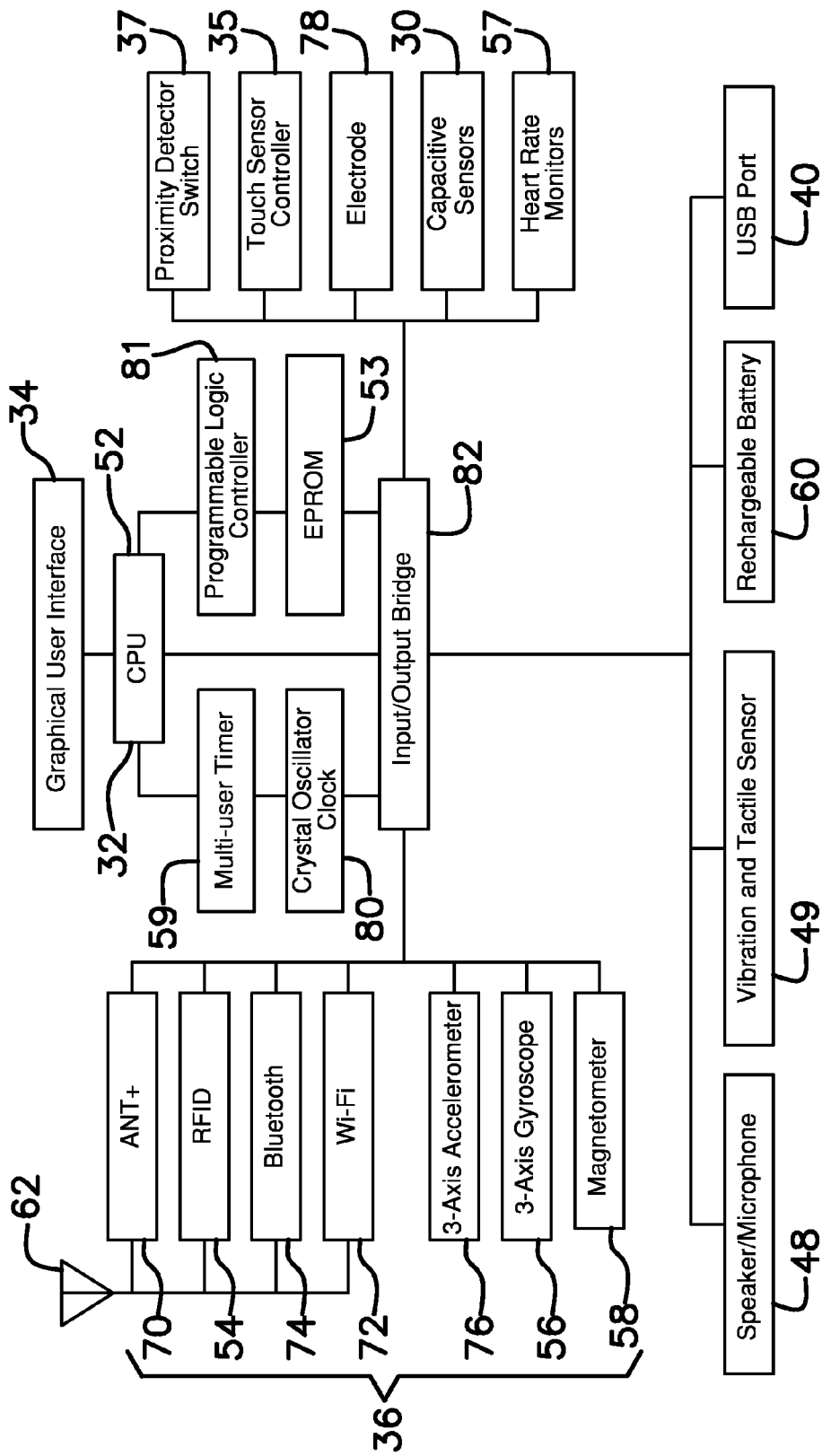
FIG. 5 is a schematic block diagram of a plurality of components and capabilities of the electronic track baton device.
Figure 6:
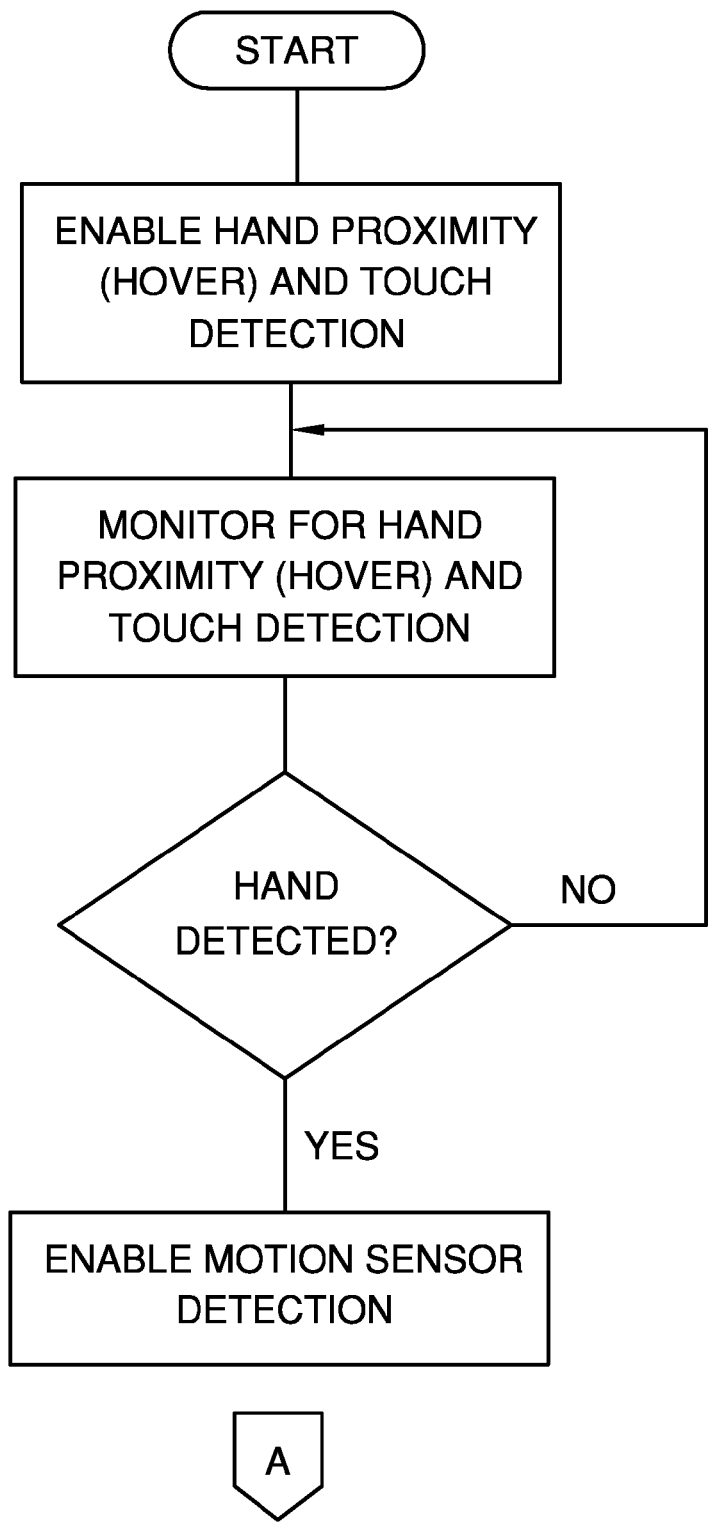
FIG. 6 is a sensing flowchart.
Figure 7:
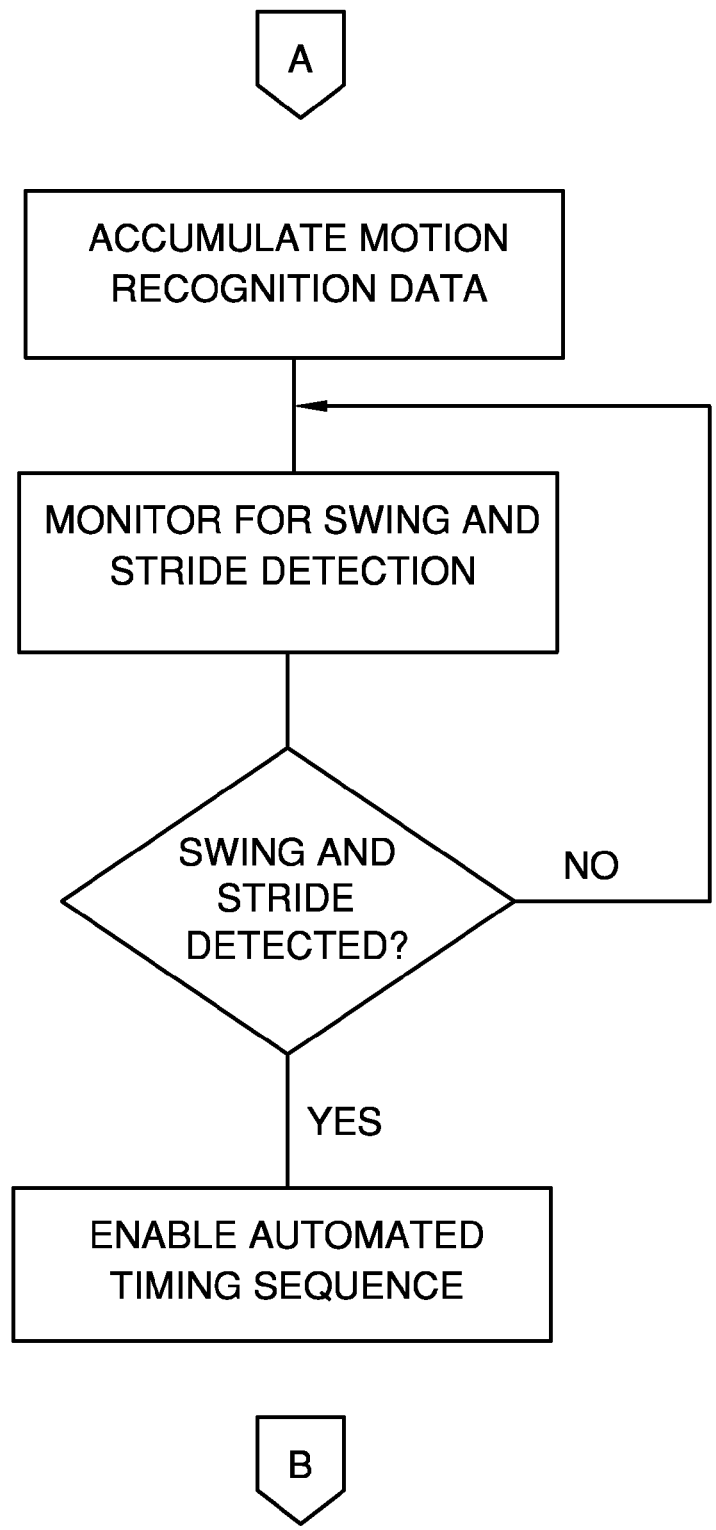
FIG. 7 is a sensing flowchart.
Figure 8:
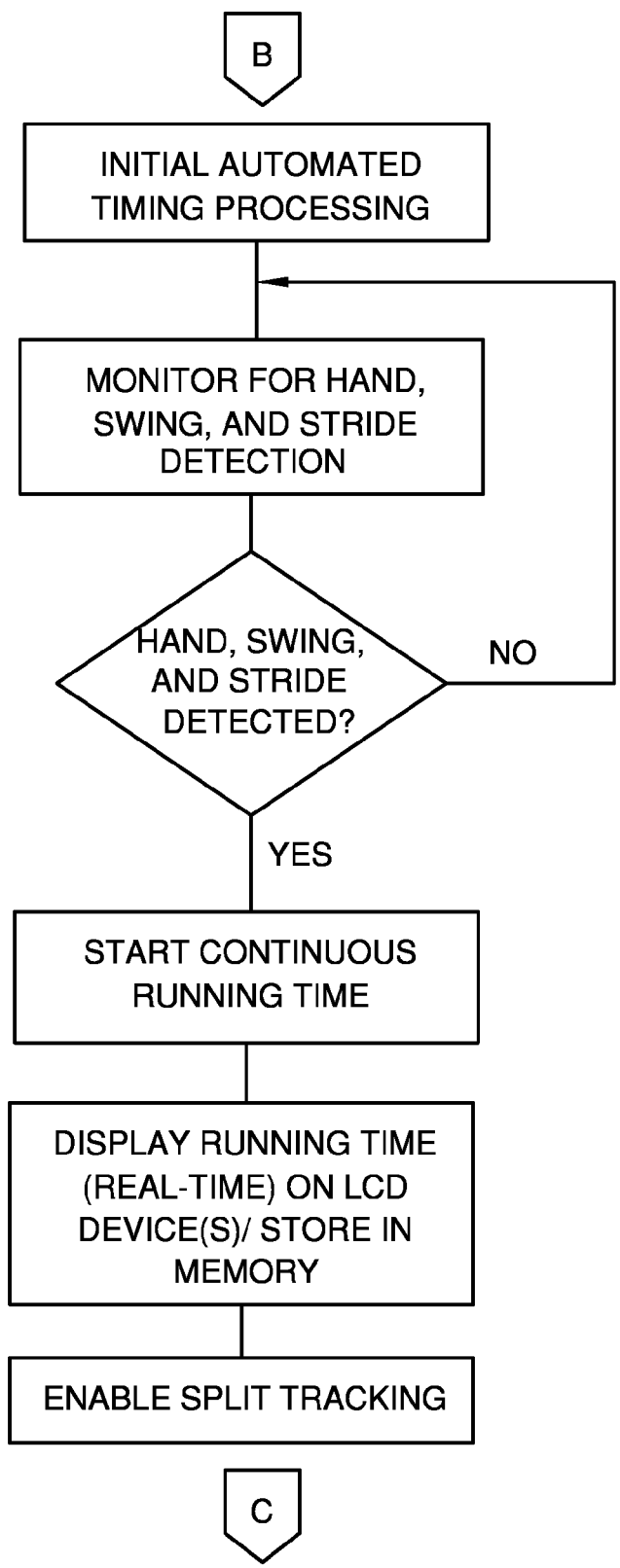
FIG. 8 is a sensing flowchart.
Figure 8A:
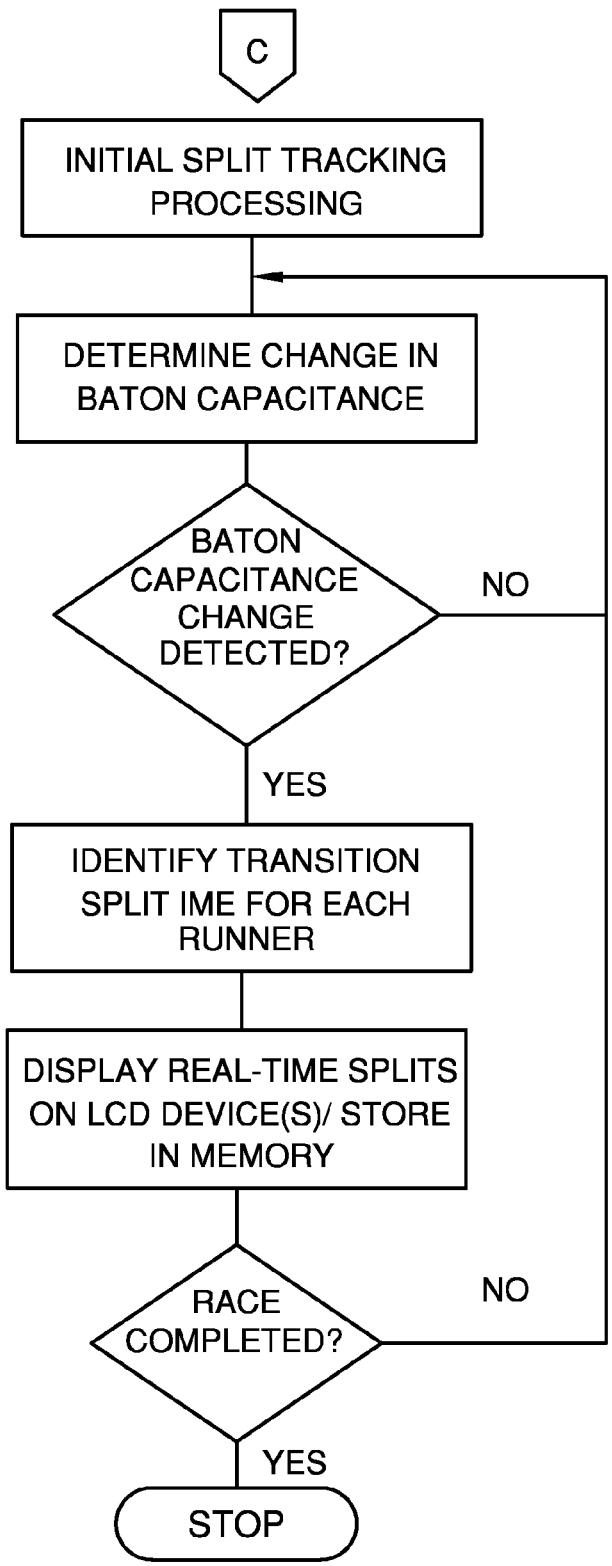
FIG. 8A is split timing flowchart.
Figure 9:
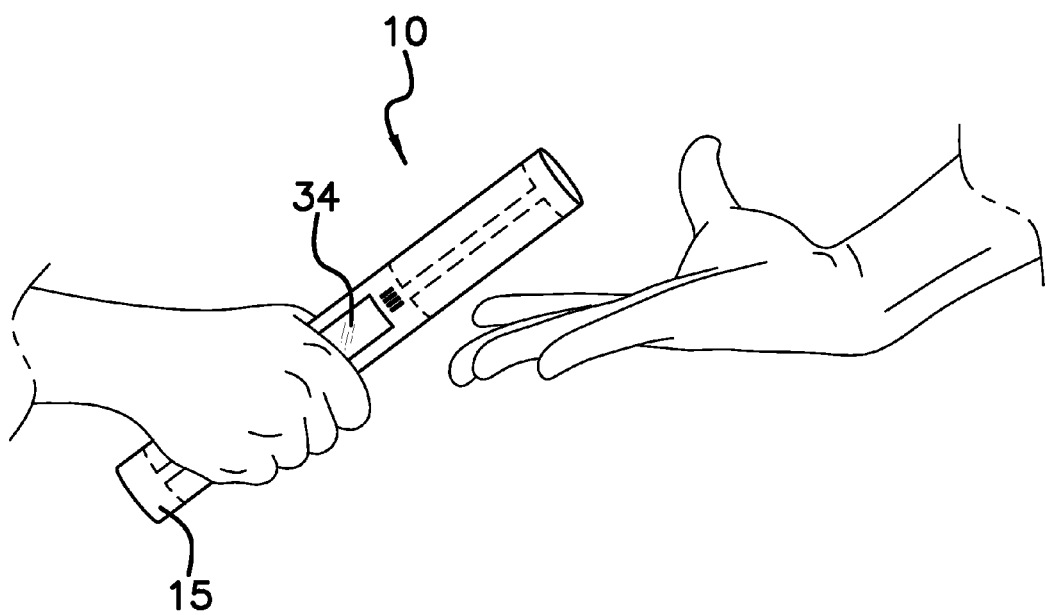
FIG. 9 is an in use view.

With reference now to the drawings, and in particular FIGS. 1 through 9 thereof, an example of the electronic track baton device employing the principles and concepts of the present electronic track baton device and generally designated by the reference number 10 will be described.

Referring to FIGS. 1 through 9, the electronic track baton device 10 is illustrated. The electronic track baton device 10 comprises a hollow cylindrical baton 15 having a first end 20 spaced apart from a second end 22, a first linear member 24 selectively separable from a second linear member 26, each of the linear members 24 and 26 extended from the first end 20 to the second end 22, a length 27 no greater than 11½ inches and a constant circumference 28 of at least 4 inches but no greater than 5 inches. A GUI 34 is disposed equidistantly between the first end 20 and the second end 22 within the first linear member 24. A touch sensor 35 is disposed within the GUI 34. A plurality of externally sensitive capacitor sensors 30 is provided. One capacitor sensor disposed between the GUI 34 and the first end 20 of each of the first linear member 24 and the second linear member 26, respectively. One capacitor sensor 30 is disposed between the GUI 34 and the second end 22 of each of the first linear member 24 and the second linear member 26, respectively. The capacitor sensors 30 comprise a biometric sensor switching 32. An existing metal in communication with the capacitor sensors 30 becomes an extension of the capacitive sensors 30. A proximity detector switch 37 is in operational communication with the capacitor sensors 30.

A plurality of interactive electronic components is disposed within the hollow cylindrical baton 15. The electronic components 50 are in operational communication and are in operational communication with the GUI 34 and the capacitor sensors 30. A power button 44 and a USB port 40 are disposed within the second end 22. The remaining electronic components are disposed within an approximate center of the hollow cylindrical baton 15. The remaining electronic components comprise a plurality of FPC 36, a speaker/microphone 48, a vibration and tactile sensor 49, an EPROM 53 disposed within the CPU 52, an RFID 54, a transceiver 62, a 3-axis gyroscope 56, a heart rate monitor 57, a magnetometer 58, a multi-user timer 59, a rechargeable battery 60, a speedometer 64, a pedometer 66, a stride measure 68, an ANT+ wireless sensor network protocol 70, a Wi-Fi 72, a Bluetooth 74, a biometric sensor switching 32, a 3-axis accelerometer 76, an electrode 78, and a crystal oscillator clock 80, a programmable logic controller 81, and an input/output bridge 82.

The track baton device 10 is configured to interact with various existing media via the Bluetooth 74, the WiFi 72, the transceiver 62, and the USB port 40. The device 10 importantly configured to provide split timing for a plurality of users via the multi-user timer 59.

What is claimed is:

1. An electronic track baton device comprising:
a hollow cylindrical baton having a first end spaced apart from a second end, a first linear member selectively separable from a second linear member, each linear member extended from the first end to the second end, a length no greater than 11½ inches and a constant circumference of at least 4 inches but no greater than 5 inches;
a GUI disposed equidistantly between the first end and the second end within the first linear member;
a touch sensor disposed within the GUI;
a plurality of externally sensitive capacitor sensors, one capacitor sensor disposed between the GUI and the first end of each of the first linear member and the second linear member, respectively, one capacitor sensor disposed between the GUI and the second end of each of the first linear member and the second linear member, respectively, the capacitor sensors comprising biometric sensor switching;
wherein any existing metal in communication with the capacitor sensors becomes an extension of the capacitive sensors;
a plurality of interactive electronic components and capabilities disposed within the hollow cylindrical baton, the electronic components in operational communication and in operational communication with the GUI, and the capacitor sensors, the electronic components and capabilities comprising but not limited to:
a plurality of FPC;
a USB port disposed within the second end;
a power button disposed within the second end;
a speaker/microphone;
a CPU;
an EPROM disposed within the CPU;
an RFID;
a vibration and tactile sensor;
a gyroscope;
a heart rate monitor;
a magnetometer;
a multi-user timer;
a rechargeable battery;
a transceiver;
a speedometer;
a pedometer;
a stride measure;
an ANT+;
a Wi-Fi capability;
a Bluetooth capability;
a 3-axis accelerometer;
an electrode;
a clock with multi-user timing;
a programmable logic controller; and
an input/output bridge;
wherein the device is configured to provide recorded playback to a plurality of users;
wherein the device is configured to interact with a plurality of existing media devices via the transceiver, Bluetooth, the WiFi, the RFID, and the USB port; and
wherein the device is configured to provide split timing for a plurality of users.

2. The device according to claim 1 wherein the touch screen is recessed.

3. The device according to claim 1 wherein the USB port and the power button are disposed about one inch within the second end.

4. The device according to claim 2 wherein the USB port and the power button are disposed about one inch within the second end.

\* \* \* \* \*